United States Patent
Capoglu et al.

(10) Patent No.: US 11,579,135 B2
(45) Date of Patent: Feb. 14, 2023

(54) SYSTEM AND METHOD FOR MEASURING MUD PROPERTIES

(71) Applicant: Halliburton Energy Services, Inc., Houston, TX (US)

(72) Inventors: Ilker R. Capoglu, Houston, TX (US); Baris Guner, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 319 days.

(21) Appl. No.: 16/652,272

(22) PCT Filed: May 14, 2019

(86) PCT No.: PCT/US2019/032253
§ 371 (c)(1),
(2) Date: Mar. 30, 2020

(87) PCT Pub. No.: WO2020/231411
PCT Pub. Date: Nov. 19, 2020

(65) Prior Publication Data
US 2021/0405016 A1    Dec. 30, 2021

(51) Int. Cl.
*G01N 33/24* (2006.01)
*E21B 47/12* (2012.01)
(Continued)

(52) U.S. Cl.
CPC ..... *G01N 33/2823* (2013.01); *E21B 47/0025* (2020.05); *G01V 3/20* (2013.01); *G01V 3/38* (2013.01)

(58) Field of Classification Search
CPC ............ G01N 33/2823; E21B 47/0025; E21B 47/00; E21B 49/00; E21B 47/022;
(Continued)

(56) References Cited

U.S. PATENT DOCUMENTS 3,060,373 A    10/1962   Doll
3,132,298 A    5/1964    Doll et al.
(Continued)

FOREIGN PATENT DOCUMENTS

CA            685727        5/1964
WO    WO-2018143946 A1 *  8/2018   ......... E21B 47/0228
(Continued)

OTHER PUBLICATIONS

ISRWO International Search Report and Written Opinion for PCT/US2019/032253 dated Aug. 24, 2016.
(Continued)

*Primary Examiner* — Jeffrey P Aiello
(74) *Attorney, Agent, or Firm* — John Wustenberg; C. Tumey Law Group PLLC

(57) ABSTRACT

A downhole tool may comprise a mandrel, wherein the mandrel is a structural support for the downhole tool; one or more arms, wherein the one or more arms are attached to the mandrel; and a pad, wherein the pad is connected to the one or more arms. The pad may comprise a material, where the material expands or contracts from an external electromagnetic field; an insulator, wherein the insulator is connected at a first end to the material; and an electrode, wherein the electrode is connected to the insulator. A method may comprise applying a time varying biasing voltage to a material, wherein the material exhibits mechanical strain; taking a first measurement and a second measurement with at least one operating frequency with an electrode; calculating a mud property based at least in part on the first measurement and the second measurement; and applying a mud effect removal algorithm to the mud property.

23 Claims, 9 Drawing Sheets

(51) Int. Cl.
*G01V 3/20* (2006.01)
*G01V 3/38* (2006.01)
*G01N 33/28* (2006.01)
*E21B 47/002* (2012.01)

(58) Field of Classification Search
CPC .......... E21B 47/113; G01V 3/20; G01V 3/38;
G01V 3/24; G01V 11/005; G01V 3/28;
G01V 3/30; G01V 3/26; G01V 3/02;
G01V 3/101; G01V 3/10; G01V
2210/6163
USPC .................. 73/152.03, 152.19; 166/250.01;
324/333, 338–339, 347, 351, 355,
324/366–367, 371, 374; 367/13, 25;
702/2–7, 11, 85
See application file for complete search history.

(56) References Cited

U.S. PATENT DOCUMENTS

| | | | |
|---|---|---|---|
| 3,379,963 | A | 4/1968 | Saurenman |
| 3,379,964 | A | 4/1968 | Segesman |
| 3,579,098 | A | 5/1971 | Mougne |
| 4,251,773 | A | 2/1981 | Cailliau et al. |
| 4,468,623 | A | 8/1984 | Gianzero et al. |
| 4,545,242 | A | 10/1985 | Chan |
| 4,567,759 | A | 2/1986 | Ekstrom et al. |
| 4,692,908 | A | 9/1987 | Ekstrom et al. |
| 4,851,781 | A | 7/1989 | Marzetta et al. |
| 4,862,090 | A | 8/1989 | Zannier et al. |
| 5,008,625 | A | 4/1991 | Chen |
| 5,012,193 | A | 4/1991 | Chen |
| 5,038,378 | A | 8/1991 | Chen |
| 6,191,588 | B1 | 2/2001 | Chen |
| RE42,493 | E | 6/2011 | Tabarovsky et al. |
| 8,579,037 | B2 | 11/2013 | Jacob |
| 8,901,933 | B2 | 12/2014 | Hayman |
| 2005/0067191 | A1* | 3/2005 | Miyamoto ............... G01V 1/52 175/50 |
| 2011/0192222 | A1 | 8/2011 | Vetter |
| 2014/0347056 | A1* | 11/2014 | Hayman ................. G01V 3/20 324/355 |
| 2017/0212269 | A1 | 7/2017 | Itskovich et al. |
| 2017/0269250 | A1 | 9/2017 | Jin et al. |
| 2018/0016888 | A1* | 1/2018 | San Martin ............ E21B 47/08 |
| 2018/0210107 | A1* | 7/2018 | Donderici ............... E21B 47/26 |
| 2018/0321411 | A1 | 11/2018 | Capoglu et al. |
| 2019/0338633 | A1 | 11/2019 | Donderici et al. |

FOREIGN PATENT DOCUMENTS

| | | |
|---|---|---|
| WO | 2019088988 | 5/2019 |
| WO | WO-2019088988 A1 * | 5/2019 |
| WO | 2019177588 | 9/2019 |

OTHER PUBLICATIONS

ISRWO International Search Report and Written Opinion for PCT/US2017/059252 dated Jul. 26, 2018.
SPWLA 61st Annual Logging Symposium, Guner, et al., Quantitative Demonstration of a High-Fidelity Oil-Based Mud Resistivity Imager using a Controlled Experiment, Jun. 24 to Jul. 29, 2020.
Chen, et al. A Novel Array Laterolog Method, Oct. 1998.
SPWLA 38th Annual Logging Symposium, Vigne, et al., Strange Invasion Profiles: What Multiarray Induction Logs can tell us about how Oil-Based Mud affects the invasion process and wellbore stability, Jun. 1997.
SPE22726, Safinya, et al., Improved Formation Imaging with Extended Microelectrical Arrays, 1991.
SPE30584, Smits, et al., High Resolution from a New Laterolog with Azimuthal Imaging, 1995.
SPE Formation Evaluation, Davies, et al., Azimuthal Resistivity Imaging: A New-Generation Laterolog, Sep. 1994.
SPE401, Suau, et al., The Dual Laterolog-R Tool, Jul. 1973.

* cited by examiner

SYSTEM AND METHOD FOR MEASURING MUD PROPERTIES

BACKGROUND

Boreholes drilled into subterranean formations may enable recovery of desirable fluids (e.g., hydrocarbons) using a number of different techniques. A downhole tool may be employed in subterranean operations to determine borehole and/or formation properties.

Traditionally, borehole imager tools may be used in obtaining a detailed characterization of reservoirs. These borehole imager tools may provide a resistivity image of the formation immediately surrounding the borehole. Borehole imager tools may be used to determine formation stratigraphy, dips of the formation layers as well as, borehole and formation stress. During drilling operations borehole imager tools may be particularly important in learning about thin beds, fracture locations, and low resistivity formations. Oil based muds may provide higher performance than the water based muds and may be preferable in deep water environments where high temperature and pressure cause loss of water and in shale zones where water may cause swelling.

However, oil based muds may be highly resistive. This resistance may contribute to the measured impedance of the formation and may affect the quality of the resistivity image obtained by oil based mud imagers. This effect may be more pronounced when standoff between the surface of the borehole imager tool and the borehole wall may be high. To remove this mud effect, presently existing processing methods may be exercised. However, these processing methods may require accurate determination of the mud angle. Improper determination of this mud angle may result in skewed measurements obtained by oil based mud imagers.

BRIEF DESCRIPTION OF THE DRAWINGS

For a detailed description of the preferred examples of the disclosure, reference will now be made to the accompanying drawings in which.

DETAILED DESCRIPTION

The present disclosure relates generally to a system and method for obtaining mud properties, including the mud angle, which may be needed to successfully execute the existing processing methods created for removing the mud effect. The purposed system and method, as a result, may increase the quality of the resistivity image obtained using oil based mud imagers. For example, the mud effect may occur when the mud used in drilling operations contributes to the measured impedance of the surrounding formation. This may decrease the correlation of the measured impedance to the formation resistivity and therefore may lower the quality of the resistivity image. Additionally, this effect may be more pronounced when standoff between the surface of the tool and the borehole wall may be high. However, the mud effect may be removed using existing processing methods that require accurate measurement of the mud angle. Thus, it may be beneficial to accurately determine the mud angle during drilling operations so that the methods used to remove the mud effect may be successfully executed.

Figure 1:
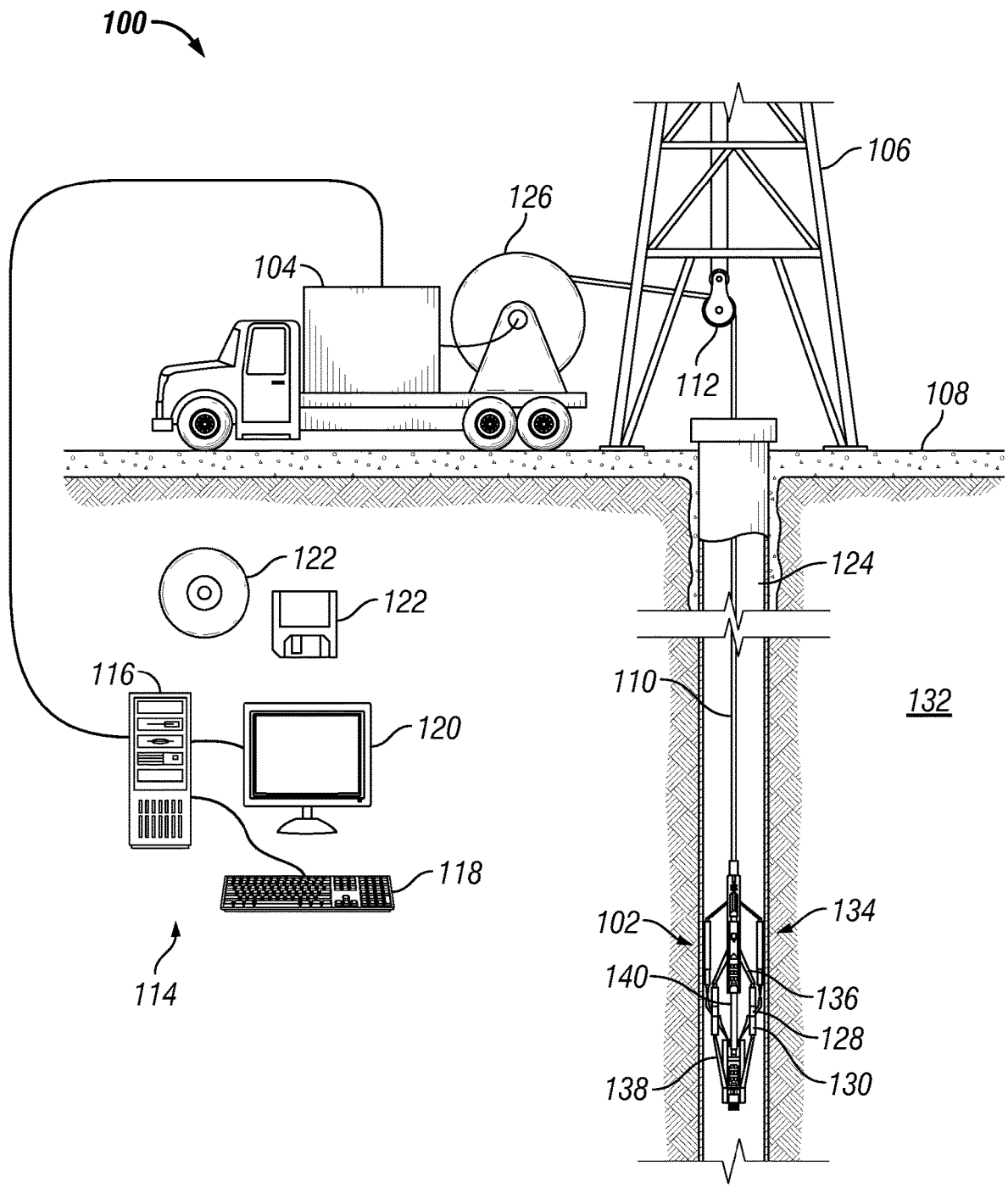
FIG. 1 illustrate an example of a well measurement system.

FIG. 1 illustrates a cross-sectional view of a well measurement system 100. As illustrated, well measurement system 100 may include downhole tool 102 attached to a vehicle 104. In examples, it should be noted that downhole tool 102 may not be attached to a vehicle 104. Downhole tool 102 may be supported by rig 106 at surface 108. Downhole tool 102 may be tethered to vehicle 104 through conveyance 110. Conveyance 110 may be disposed around one or more sheave wheels 112 to vehicle 104. Conveyance 110 may include any suitable means for providing mechanical conveyance for downhole tool 102, including, but not limited to, wireline, slickline, coiled tubing, pipe, drill pipe, drill string, downhole tractor, or the like. In some examples, conveyance 110 may provide mechanical suspension, as well as electrical connectivity, for downhole tool 102.

Conveyance 110 may include, in some instances, a plurality of electrical conductors extending from vehicle 104. Conveyance 110 may include an inner core of seven electrical conductors covered by an insulating wrap. An inner and outer steel armor sheath may be wrapped in a helix in opposite directions around the conductors. The electrical conductors may be used for communicating power and telemetry between vehicle 104 and downhole tool 102.

Conveyance 110 may lower downhole tool 102 in borehole 124. Generally, borehole 124 may include horizontal, vertical, slanted, curved, and other types of borehole geometries and orientations. Imaging tools may be used in uncased sections of the borehole. Measurements may be made by downhole tool 102 in cased sections for purposes such as calibration.

As illustrated, borehole 124 may extend through formation 132. As illustrated in FIG. 1, borehole 124 may extend generally vertically into the formation 132, however borehole 124 may extend at an angle through formation 132, such as horizontal and slanted boreholes. For example, although FIG. 1 illustrates a vertical or low inclination angle well, high inclination angle or horizontal placement of the well and equipment may be possible. It should further be noted that while FIG. 1 generally depicts a land-based operation, those skilled in the art may recognize that the principles described herein are equally applicable to subsea operations that employ floating or sea-based platforms and rigs, without departing from the scope of the disclosure.

Information from downhole tool 102 may be gathered and/or processed by information handling system 114. For example, signals recorded by downhole tool 102 may be stored on memory and then processed by downhole tool 102. The processing may be performed real-time during data acquisition or after recovery of downhole tool 102. Processing may alternatively occur downhole or may occur both downhole and at surface. In some examples, signals recorded by downhole tool 102 may be conducted to information handling system 114 by way of conveyance 110. Information handling system 114 may process the signals, and the information contained therein may be displayed for an operator to observe and stored for future processing and reference. Information handling system 114 may also contain an apparatus for supplying control signals and power to downhole tool 102.

Systems and methods of the present disclosure may be implemented, at least in part, with information handling system 114. While shown at surface 108, information handling system 114 may also be located at another location, such as remote from borehole 124. Information handling system 114 may include any instrumentality or aggregate of instrumentalities operable to compute, estimate, classify, process, transmit, receive, retrieve, originate, switch, store, display, manifest, detect, record, reproduce, handle, or utilize any form of information, intelligence, or data for business, scientific, control, or other purposes. For example, an information handling system 114 may be a processing unit 116, a network storage device, or any other suitable device and may vary in size, shape, performance, functionality, and price. Information handling system 114 may include random access memory (RAM), one or more processing resources such as a central processing unit (CPU) or hardware or software control logic, ROM, and/or other types of nonvolatile memory. Additional components of the information handling system 114 may include one or more disk drives, one or more network ports for communication with external devices as well as an input device 118 (e.g., keyboard, mouse, etc.) and video display 120. Information handling system 114 may also include one or more buses operable to transmit communications between the various hardware components.

Alternatively, systems and methods of the present disclosure may be implemented, at least in part, with non-transitory computer-readable media 122. Non-transitory computer-readable media 122 may include any instrumentality or aggregation of instrumentalities that may retain data and/or instructions for a period of time. Non-transitory computer-readable media 122 may include, for example, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory (EEPROM), and/or flash memory; as well as communications media such as wires, optical fibers, microwaves, radio waves, and other electromagnetic and/or optical carriers; and/or any combination of the foregoing.

As discussed below, methods may utilize an information handling system 114 to determine and display a high resolution resistivity image of formation 132 immediately surrounding borehole 124. This high resolution resistivity image may depict boundaries of subsurface structures, such as a plurality of layers disposed in formation 132. These formation images may be used in reservoir characterization. Formation images with high resolution may allow accurate identification of thin beds and other fine features such as fractures, clasts and vugs. These formation images may provide information about the sedimentology, lithology, porosity and permeability of formation 132. The formation images may complement, or in some cases replace, the process of coring.

In examples, rig 106 includes a load cell (not shown) which may determine the amount of pull on conveyance 110 at the surface of borehole 124. Information handling system 114 may include a safety valve which controls the hydraulic pressure that drives drum 126 on vehicle 104 which may reel up and/or release conveyance 110 which may move downhole tool 102 up and/or down borehole 124. Conveyance 110 may provide a means of disposing downhole tool 102 into borehole 124. The safety valve may be adjusted to a pressure such that drum 126 may only impart a small amount of tension to conveyance 110 over and above the tension necessary to retrieve conveyance 110 and/or downhole tool 102 from borehole 124. The safety valve is typically set a few hundred pounds above the amount of desired safe pull on conveyance 110 such that once that limit is exceeded; further pull on conveyance 110 may be prevented.

Downhole tool 102 may include a plurality of electrodes, such as button array 128. Downhole tool 102 may also include a return electrode 130. It should be noted that the plurality of electrodes disposed on button array 128 may be any suitable electrode and is should be further noted that return electrode 130 may be any suitable electrode. Button array 128 and/or return electrode 130 may be disposed on at least one pad 134 in any suitable order. For example, a pad 134 may include only button arrays 128 and/or return electrodes 130. Further, a pad 134 may include both button array 128 and return electrodes 130. Pads 134 may attach to a mandrel 140 of downhole tool 102 through upper arm 136 and lower arm 138. It should be noted that mandrel 140 may be defined as the supporting structure of downhole tool 102 which may act as a platform for any peripheral (e.g., upper arm 136, lower arm 138, conveyance 110, etc.) to attach to downhole tool 102. Upper arm 136 and lower arm 138 may extend pad 134 away from downhole tool 102. In examples, both upper arm 136 and lower arm 138 may place pad 134 in contact with borehole 124. It should be noted that there may be any suitable number of arms and/or extensions that may be used to move pad 134 away from downhole tool 102 and in close proximity with borehole 124, or vice versa.

During operations, an operator may energize an individual electrode, or any number of electrodes, of button array 128. A voltage may be applied between the electrode and return electrode 130. The level of the voltage may be controlled by information handling system 114. This may cause currents to be transmitted through the electrode of button array 128. It should be noted that there may be any number of currents transmitted into formation 132. These currents may travel through the mud disposed in borehole 124 and formation 132 and may reach back to return electrode 130. The amount of current emitted by each electrode may be inversely proportional to the impedance seen by the electrode. This impedance may be affected by the properties of formation 132 and the mud directly in front of each electrode of button array 128. Therefore, current emitted by each electrode may be measured and recorded in order to obtain a formation image of the resistivity of formation 132.

To produce a resistivity image of formation 132, a current may be transmitted from at least one transmitter electrode and return to return electrode 130. These two electrodes may be referred to as the current electrodes. Then, the voltage drop across a pair of the electrodes of button array 128 may be measured and used to estimate the impedance of formation 132. In these alternative implementations, button electrodes may be referred to as voltage electrodes or monitor electrodes. Proposed method may operate in any of the two designs above or any other similar oil based mud resistivity imager tool without any limitations.

In examples, downhole tool 102 may operate with additional equipment (not illustrated) on surface 108 and/or disposed in a separate well measurement system (not illustrated) to record measurements and/or values from formation 132 to render a resistivity image of formation 132. Without limitation, downhole tool 102 may be connected to and/or controlled by information handling system 114, which may be disposed on surface 108. Without limitation, information handling system 114 may be disposed down hole in downhole tool 102. Processing of information recorded may occur down hole and/or on surface 108. In addition to, or in place of processing at surface 108, processing may occur downhole. Processing occurring downhole may be transmitted to surface 108 to be recorded, observed, and/or further analyzed. Additionally, information recorded on information handling system 114 that may be disposed down hole may be stored until downhole tool 102 may be brought to surface 108. In examples, information handling system 114 may communicate with downhole tool 102 through a fiber optic cable (not illustrated) disposed in (or on) conveyance 110. In examples, wireless communication may be used to transmit information back and forth between information handling system 114 and downhole tool 102. Information handling system 114 may transmit information to downhole tool 102 and may receive as well as process information recorded by downhole tool 102. In examples, a downhole information handling system (not illustrated) may include, without limitation, a microprocessor or other suitable circuitry, for estimating, receiving and processing signals from downhole tool 102. Downhole information handling system (not illustrated) may further include additional components, such as memory, input/output devices, interfaces, and the like. In examples, while not illustrated, downhole tool 102 may include one or more additional components, such as analog-to-digital converter, filter and amplifier, among others, that may be used to process the measurements of downhole tool 102 before they may be transmitted to surface 108. Alternatively, raw measurements from downhole tool 102 may be transmitted to surface 108.

Any suitable technique may be used for transmitting signals from downhole tool 102 to surface 108. As illustrated, a communication link (which may be wired or wireless and may be disposed in conveyance 110, for example) may be provided that may transmit data from downhole tool 102 to an information handling system 114 at surface 108.

Figure 2:
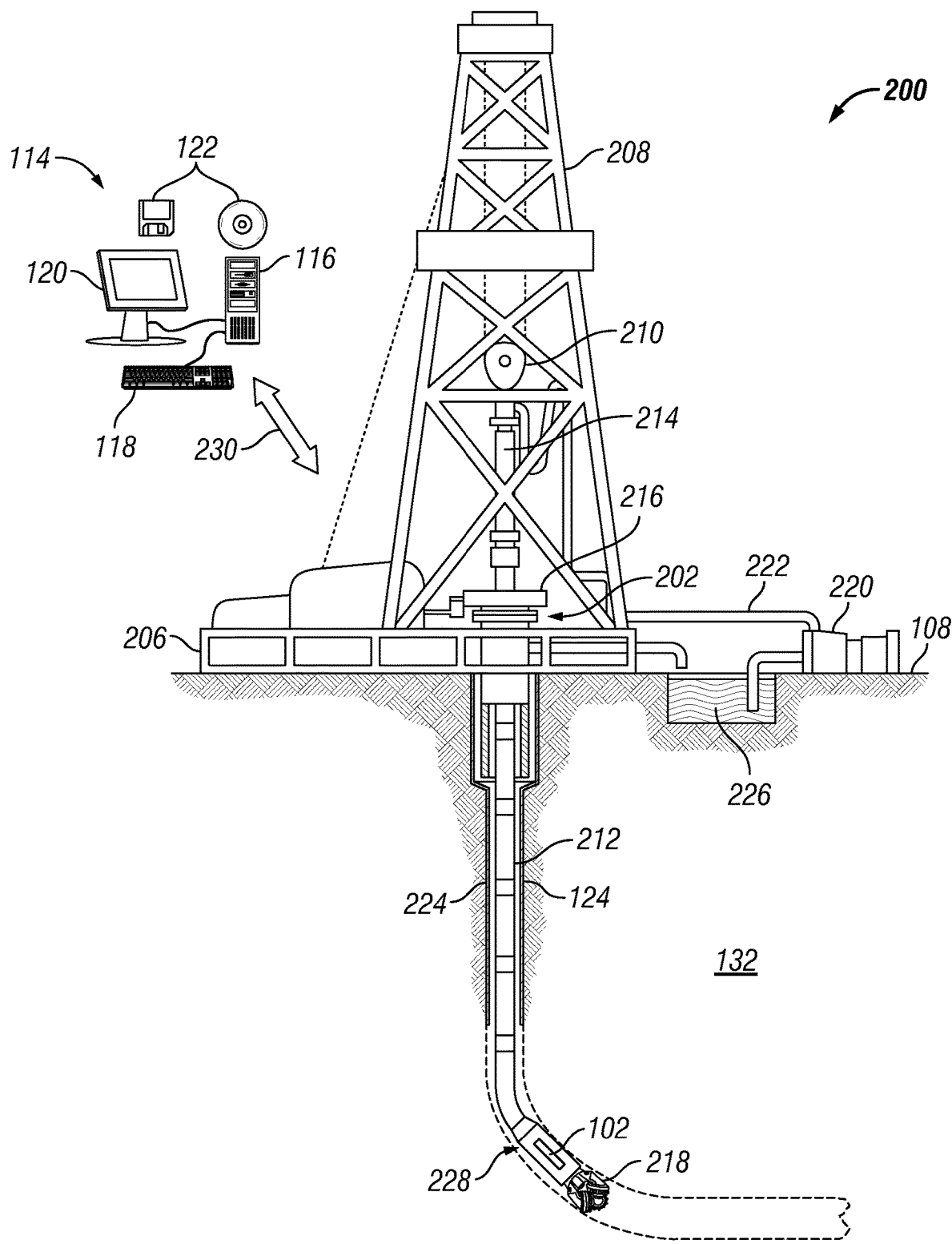
FIG. 2 illustrates another example of a well measurement system.

FIG. 2 illustrates an example in which downhole tool 102 (Referring to FIG. 1) may be disposed in a drilling system 200. As illustrated, borehole 124 may extend from a wellhead 202 into formation 132 from surface 108. As illustrated, a drilling platform 206 may support a derrick 208 having a traveling block 210 for raising and lowering drill string 212. Drill string 212 may include, but is not limited to, drill pipe and coiled tubing, as generally known to those skilled in the art. A kelly 214 may support drill string 212 as it may be lowered through a rotary table 216. A drill bit 218 may be attached to the distal end of drill string 212 and may be driven either by a downhole motor and/or via rotation of drill string 212 from surface 108. Without limitation, drill bit 218 may include, roller cone bits, PDC bits, natural diamond bits, any hole openers, reamers, coring bits, and the like. As drill bit 218 rotates, it may create and extend borehole 124 that penetrates various formations 132. A pump 220 may circulate drilling fluid through a feed pipe 222 to kelly 214, downhole through interior of drill string 212, through orifices in drill bit 218, back to surface 108 via annulus 224 surrounding drill string 212, and into a retention pit 226.

With continued reference to FIG. 2, drill string 212 may begin at wellhead 202 and may traverse borehole 124. Drill bit 218 may be attached to a distal end of drill string 212 and may be driven, for example, either by a downhole motor and/or via rotation of drill string 212 from surface 108 (Referring to FIG. 1). Drill bit 218 may be a part of bottom hole assembly 228 at distal end of drill string 212. Bottom hole assembly 228 may further include downhole tool 102 (Referring to FIG. 1). Downhole tool 102 may be disposed on the outside and/or within bottom hole assembly 228. Downhole tool 102 may include test cell 234. As will be appreciated by those of ordinary skill in the art, bottom hole assembly 228 may be a measurement—while drilling (MWD) or logging-while-drilling (LWD) system.

Without limitation, bottom hole assembly 228 may be connected to and/or controlled by information handling system 114 (Referring to FIG. 1), which may be disposed on surface 108. Without limitation, information handling system 114 may be disposed down hole in bottom hole assembly 228. Processing of information recorded may occur down hole and/or on surface 108. Processing occurring downhole may be transmitted to surface 108 to be recorded, observed, and/or further analyzed. Additionally, information recorded on information handling system 114 that may be disposed down hole may be stored until bottom hole assembly 228 may be brought to surface 108. In examples, information handling system 114 may communicate with bottom hole assembly 228 through a fiber optic cable (not illustrated) disposed in (or on) drill string 212. In examples, wireless communication may be used to transmit information back and forth between information handling system 114 and bottom hole assembly 228. Information handling system 114 may transmit information to bottom hole assembly 228 and may receive as well as process information recorded by bottom hole assembly 228. In examples, a downhole information handling system (not illustrated) may include, without limitation, a microprocessor or other suitable circuitry, for estimating, receiving and processing signals from bottom hole assembly 228. Downhole information handling system (not illustrated) may further include additional components, such as memory, input/output devices, interfaces, and the like. In examples, while not illustrated, bottom hole assembly 228 may include one or more additional components, such as analog-to-digital converter, filter and amplifier, among others, that may be used to process the measurements of bottom hole assembly 228 before they may be transmitted to surface 108. Alternatively, raw measurements from bottom hole assembly 228 may be transmitted to surface 108.

Any suitable technique may be used for transmitting signals from bottom hole assembly 228 to surface 108, including, but not limited to, wired pipe telemetry, mud-pulse telemetry, acoustic telemetry, and electromagnetic telemetry. While not illustrated, bottom hole assembly 228 may include a telemetry subassembly that may transmit telemetry data to surface 108. Without limitation, an electromagnetic source in the telemetry subassembly may be operable to generate pressure pulses in the drilling fluid that propagate along the fluid stream to surface 108. At surface 108, pressure transducers (not shown) may convert the pressure signal into electrical signals for a digitizer (not illustrated). The digitizer may supply a digital form of the telemetry signals to information handling system 114 via a communication link 230, which may be a wired or wireless link. The telemetry data may be analyzed and processed by information handling system 114.

As illustrated, communication link 230 (which may be wired or wireless, for example) may be provided that may transmit data from bottom hole assembly 228 to an information handling system 114 at surface 108. Information handling system 114 may include a processing unit 116 (Referring to FIG. 1), a video display 120 (Referring to FIG. 1), an input device 118 (e.g., keyboard, mouse, etc.) (Referring to FIG. 1), and/or non-transitory computer-readable media 122 (e.g., optical disks, magnetic disks) (Referring to FIG. 1) that may store code representative of the methods described herein. In addition to, or in place of processing at surface 108, processing may occur downhole.

Figure 3:
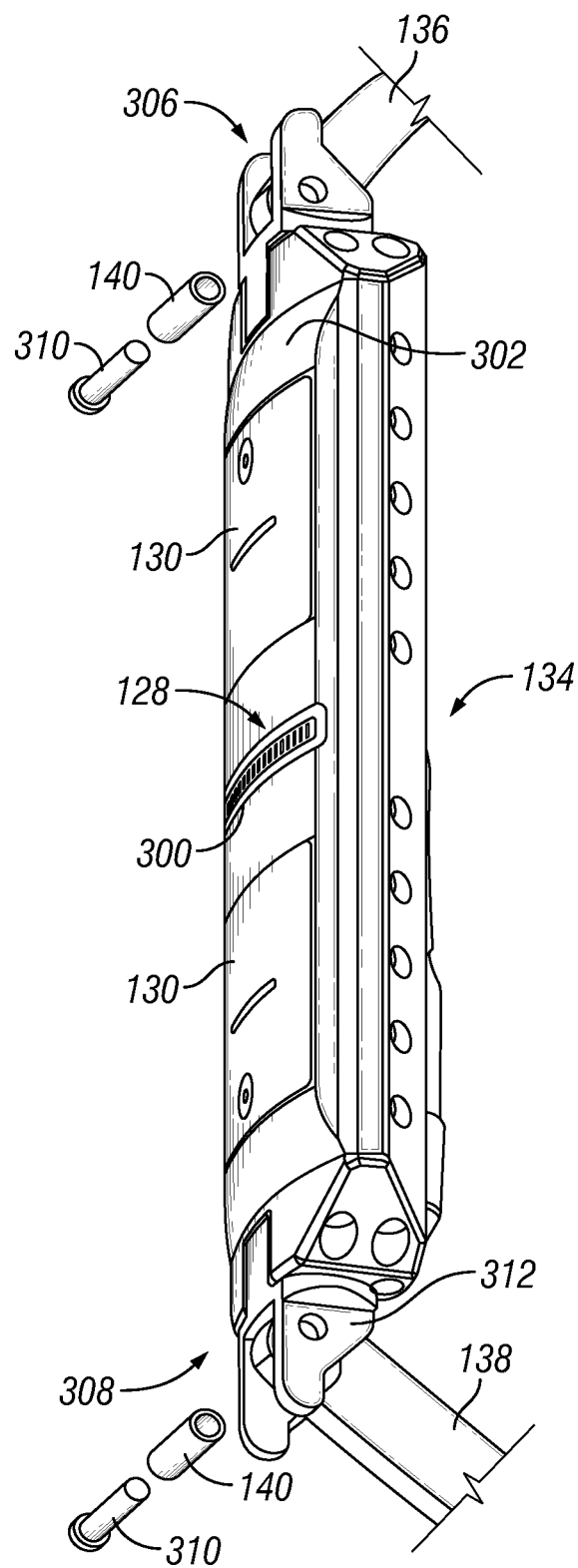
FIG. 3 illustrates an example of a pad.

FIG. 3 illustrates an example of pad 134. It should be noted that pad 134 may be connected to downhole tool 102 (e.g., referring to FIGS. 1 and 2). Pad 134 may serve to place button array 128 and/or return electrode 130 in contact with or in close proximity to borehole 124. Pad 134 may include a button array 128, a return electrode 130, a guard 300, and a housing 302. In examples, there may be a plurality of button arrays 128. In examples, return electrode 130 and button array 128 may be disposed directly on downhole tool 102. Button array 128 may include an injector electrode 304, wherein injector electrode 304 may be a sensor that senses impedance of formation 132. It should be noted that injector electrode 304 may be a button electrode. There may be any suitable number of injector electrodes 304 within button array 128 that may produce a desired, predetermined current. Without limitation, the range for a suitable number of injector electrodes 304 within button array 128 may be from about one injector electrode 304 to about one hundred injector electrodes 304. For example, the range for a suitable number of injector electrodes 304 within button array 128 may be from about one injector electrode 304 to about twenty-five injector electrodes 304, from about twenty-five injector electrodes 304 to about fifty injector electrodes 304, from about fifty injector electrodes 304 to about seventy-five injector electrodes 304, or from about seventy-five injector electrodes 304 to about one hundred injector electrodes 304.

In examples, there may be a plurality of return electrodes 130. One of the return electrodes 130 may be disposed on one side of button array 128, and another one of the return electrodes 130 may be disposed on the opposite side of button array 128. These return electrodes 130 may be disposed at equal distances away from button array 128 or at varying distances from button array 128. Without limitation, the distance from the center of one of the return electrodes to the button array may be from about one inch to about one foot. In examples, a voltage difference between button array 128 and return electrodes 130 may be applied, which may cause currents to be emitted from button array 128 into the mud (not illustrated) and formation 132 (referring to FIG. 1).

During operations, an operator may energize button array 128. A voltage may be applied between each injector electrode 304 and return electrode 130. The level of the voltage may be controlled by information handling system 114. This may cause currents to be transmitted through button array 128. These currents may travel through the mud and formation 132 and may reach back to return electrode 130. The amount of current emitted by each injector electrode 304 may be inversely proportional to the impedance seen by that injector electrode 304. This impedance may be affected by the properties of formation 132 and the mud directly in front of each injector electrode 304. Therefore, current emitted by each injector electrode 304 may be measured and recorded in order to obtain an image of the resistivity of formation 132.

In examples, a current may be transmitted from injector electrode 304 and return to return electrode 130. These two electrodes may be referred to as the current electrodes. Then, the voltage drop across button array 128 may be measured and used to estimate the impedance of formation 132. In these alternative implementations, injector electrodes 304 may be referred to as voltage electrodes or monitor electrodes. Proposed method may operate in any of the two designs above or any other similar oil based mud resistivity imager tool without any limitations. In the rest of the text, the imager tool will be assumed to be of the first design without any loss of generality.

Guard 300 may help to focus most of the current produced by button array 128 into formation 132 radially. Guard 300 may be disposed around button array 128. Guard 300 may include the same potential as button array 128.

In examples, housing 302 may serve to protect button array 128 and return electrodes 130 from the surrounding mud and formation 132. Housing may be made with any suitable material. Without limitation, suitable material may include metals, nonmetals, plastics, ceramics, composites and/or combinations thereof. In examples, housing 302 may be a metal plate. Housing 302 may be connected through upper arm 136 to downhole tool 102 (e.g., referring to FIG. 1). An insulating material may be used to fill the remaining portions of pad 134. In examples, ceramics may be used as the insulating material to fill the remaining portions of pad 134.

An impedance value may be calculated through the current transmitting between an injector electrode 304 and formation 132 for each injector electrode 304. The voltage between button array 128 and return electrodes 130 may be measured and divided by the transmitted current to produce a value for the impedance seen by each injector electrode 304. Most of the transmitted current may be returned to return electrodes 130 although some portions of it may return through housing 302 and downhole tool 102 (referring to FIG. 1).

Figure 4:
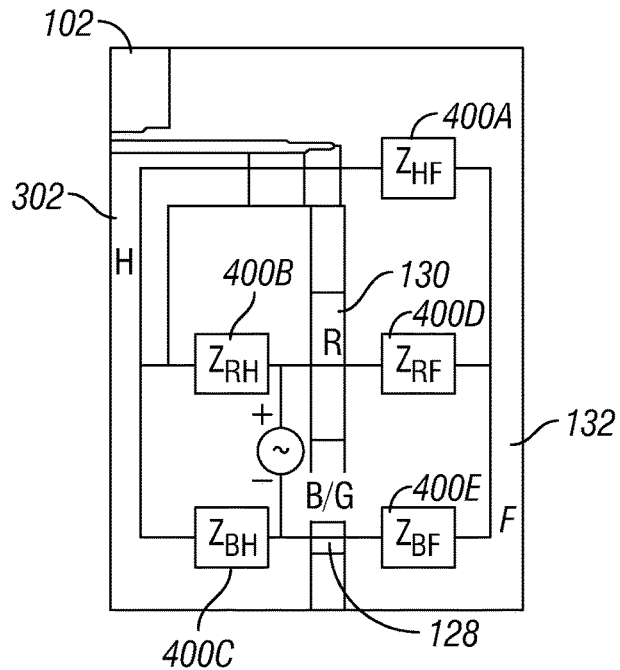
FIG. 4 illustrates an example of a circuit model of a downhole tool.

FIG. 4 illustrates an example of a circuit model that may approximate downhole tool 102. Effects of the transmitted current may be approximately characterized by a housing-to-formation impedance value 400A, a return electrode-to-housing impedance value 400B, a return electrode-to-formation impedance value 400C, a button-to-housing impedance value 400D, and a button-to-formation impedance value 400E. Impedance may be calculated below, wherein Z is the impedance, $V_{BR}$ is the button to return electrode voltage and $I_B$ is the button current:

$$Z = \frac{V_{BR}}{I_B} \tag{1}$$

The value calculated in Equation (1) may be equal to $Z_{BF}+Z_{RF}$ if impedances representing leakage through housing are ignored, as shown in FIG. 4, wherein $Z_{BF}$ is the impedance from an individual button of button array 128 to formation 132 and $Z_{RF}$ is the impedance of return electrode 130 to formation 132. It should be noted that impedances for each button of button array 128 may differ based on variations in borehole 124 and the environment. These variations in measured impedances, which may be illustrated in an impedance image, may be used to determine geophysical features. Additionally, both $Z_{BF}$ and $Z_{RF}$ have contributions from both the surrounding mud and formation 132 (referring to FIG. 1), and in general $Z_{BF}$ is much greater than $Z_{RF}$ due to the large physical size of the return. Thus, equivalently it may be written in Equation (2) as:

$$Z \approx Z_{BF} = Z_{mud} + Z_F \quad (2)$$

As a result, measured impedance may have contributions from both the mud and formation 132, wherein $Z_{mud}$ is the impedance of the mud and $Z_F$ is the impedance of formation 132. Imaginary parts of $Z_F$ and $Z_{mud}$ may be assumed to be mainly capacitive. Assuming this capacitance may be in parallel with the resistive portion, then $Z_{BF}$ may also be written as:

$$Z_{BF} = \frac{1}{\left(\frac{1}{R_M} + j\omega C_M\right)} + \frac{1}{\left(\frac{1}{R_F} + j\omega C_F\right)} \quad (3)$$

wherein $R_M$ is the mud resistance, $R_F$ is the resistance of formation 132, $C_M$ is the mud capacitance, $C_F$ is the capacitance of formation 132, j is the unit imaginary number, and ω is the angular frequency. Both the mud resistance and mud capacitance may increase as standoff increases and may decrease with the increase in effective area of button array 128. "Standoff" may be used to denote the distance of the elements of a pad 134 from a wall of borehole 124 (e.g., Referring to FIG. 1). Standoff of each individual button in a button array may vary; standoffs of the return electrodes may differ from those of the buttons as well. Standoff variations will significantly affect button to formation impedance value 400E. In the simplified circuit model, it is assumed that the standoff of each element of the pad is constant. Standoff may assume that pad 134 is movable while downhole tool 102 remains immobile. In examples, to achieve large distances from the wall of borehole 124, downhole tool 102 may be moved along with pad 134. In examples, the term "eccentricity" may be used instead of "standoff". The proposed methods (discussed further below) may be equally valid whether pad 134 moves or both pad 134 and downhole tool 102 move.

Figure 5:
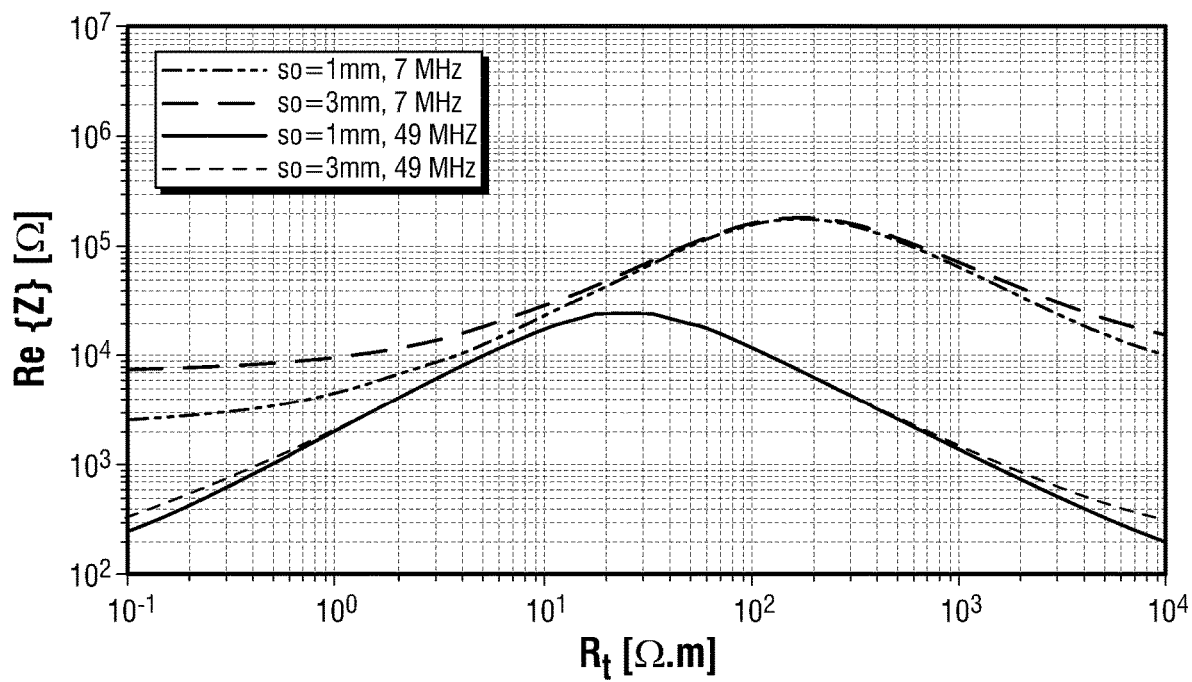
FIG. 5 illustrates a graph of the real part of the measured impedance versus the formation resistivity.

Equation (3) may be used to obtain basic performance curves for downhole tool 102. These basic performance curves may be fairly accurate in homogeneous formations 132 in determining the variation of the response of an exemplary injector electrode 304 in button array 128 (e.g., referring to FIGS. 1-3) with changing environmental parameters. In FIG. 5, the real part of the measured impedance versus the formation resistivity may be determined using Equation (3), which is illustrated on graph 500 in FIG. 5. The imaginary part of the impedance may be determined by the mud capacitance, therefore, it may not be necessary to plot it. In an example, illustrated in FIG. 5, it may be assumed that formation permittivity (εF) is 15, mud permittivity (εM) is 6, and mud resistivity (ρM) is 8000Ω·m. Results for two different frequencies (7 MHz and 49 MHz) at two different standoffs (1 mm and 3 mm) are displayed in FIG. 5. It should be noted that in the example, illustrated by FIG. 5, it may be assumed that all of pad 134 (e.g., referring to FIG. 1) may be the same distance from the wall of borehole 124 (e.g., referring to FIG. 1). In other examples, standoffs between each button of button array 128 (e.g., referring to FIG. 1) may vary. Additionally, the distance of return electrodes 130 (e.g., referring to FIG. 1) from the wall of borehole 124 may be different from the buttons of button array 128 standoff because pad 134 may be slightly tilted and/or borehole 124 may be rugose.

As illustrated in FIG. 5, as the formation resistivity decreases the mud effect may become dominant and measured impedance may become mostly flat. This is particularly pronounced at the lower frequency, 7 MHz, where measured impedance to formation resistivity curve starts to deviate significantly from linear under a formation resistivity of 10 Ohm-m and becomes almost totally flat when formation resistivity is under 1 Ohm-m when the standoff is 3 mm. Conversely, a roll-off effect may be observed where impedance may peak and then may drop to a negative range when formation 132 (e.g. referring to FIG. 1) may be measuring high resistivities. This effect is more pronounced at the higher frequency, 49 MHz, (e.g., rolloff occurs earlier.) Response starts to flatten around 15 Ohm-m at 7 MHz and 150 Ohm-m at 49 MHz. In the middle range, where there may be no mud or dielectric effect, a linear relationship between impedance and formation resistivity may be observed: $R_f = FZ$. This linear relationship may allow easy conversion from measured impedance to formation resistivity, it may result in a resistivity image with more equal color distributions and more contrast, and it may ensure image sensitivity in all formation resistivity ranges. For these reasons, it may be desirable to obtain a response that may be linearly proportional to the formation resistivity. Use of multiple frequencies may allow an operator to extend the linear range to lower/higher resistivities as may be seen in FIG. 5. However, for formation resistivities lower than ~1 Ohm, even the highest frequency may exhibit non-linear behavior. This behavior may be alleviated by introducing more frequencies. However, practical design considerations for oil based mud imagers may limit the number of frequencies, and furthermore, frequencies above 50 MHz may be difficult to work with as far as downhole electrical components are concerned.

As described above, operating in a linear region of a curve may allow for accurate correspondence between the real part of the impedance image and that of the true formation resistivity. Standoff effect at low formation resistivities may cause an ambiguity in the interpretation of the impedance images. Small errors in standoff measurements may cause a large difference in the impedance reading if these raw measurements may be used. By reducing the mud effect in the raw measurements, the response may become linear.

Figure 6:
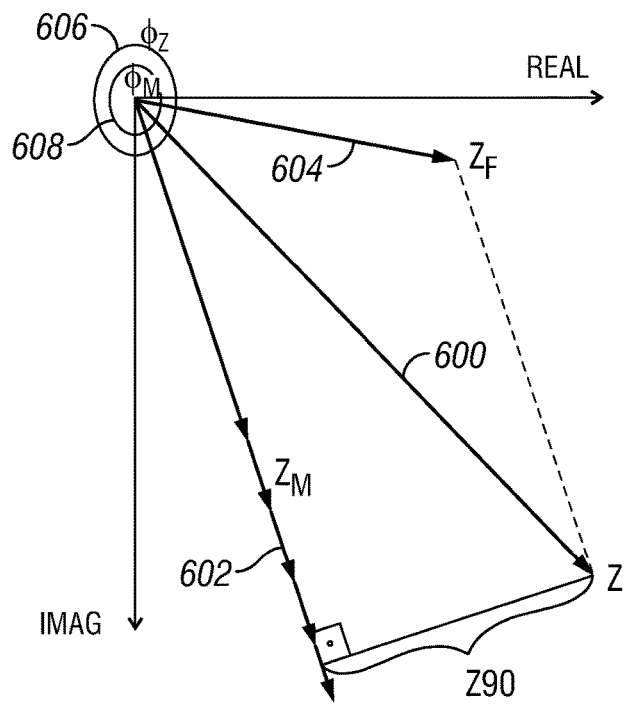
FIG. 6 illustrates an example of a Z90 processing algorithm.

In examples, a method may be used that makes use of data obtained at different standoff values to calculate the mud angle. The mud angle may be the phase angle of the impedance of the mud. In examples, the mud angle may be the arctangent of the ratio of the imaginary and the real parts of the complex impedance. In examples, the mud angle may be different at each operating frequency. The mud angle may be used in mud removal schemes to eliminate the effect of the mud (or equivalently the standoff). Without limitations, an example of such a scheme may be the Z90 algorithm, as illustrated in FIG. 6. However, any other suitable mud removal scheme may be used in examples. The Z90 algorithm may be written in Equation (4) as:

$$Z90 = |Z| \sin(\phi_Z - \phi_M) \quad (4)$$

The objective of Z90 processing may be to subtract the projection of the measured impedance on the mud impedance vector from the measured impedance to reduce the mud effect. As illustrated, measured impedance (Z), mud impedance (ZM), and formation impedance (ZF) may be represented as vector 600, vector 602, and vector 604 respectively, in the complex plane. Although the approximate direction of vector 602 may be known if the mud angle is known, its absolute strength depends on standoff among other factors. However, a projection of vector 600 onto vector 602 may be calculated accurately by measuring a phase angle of the measurement 606 and a phase angle of the mud 608. In equations, the phase angle of the measurement is defined as (φZ) while (φM) is the phase angle of the mud.

Figure 7:
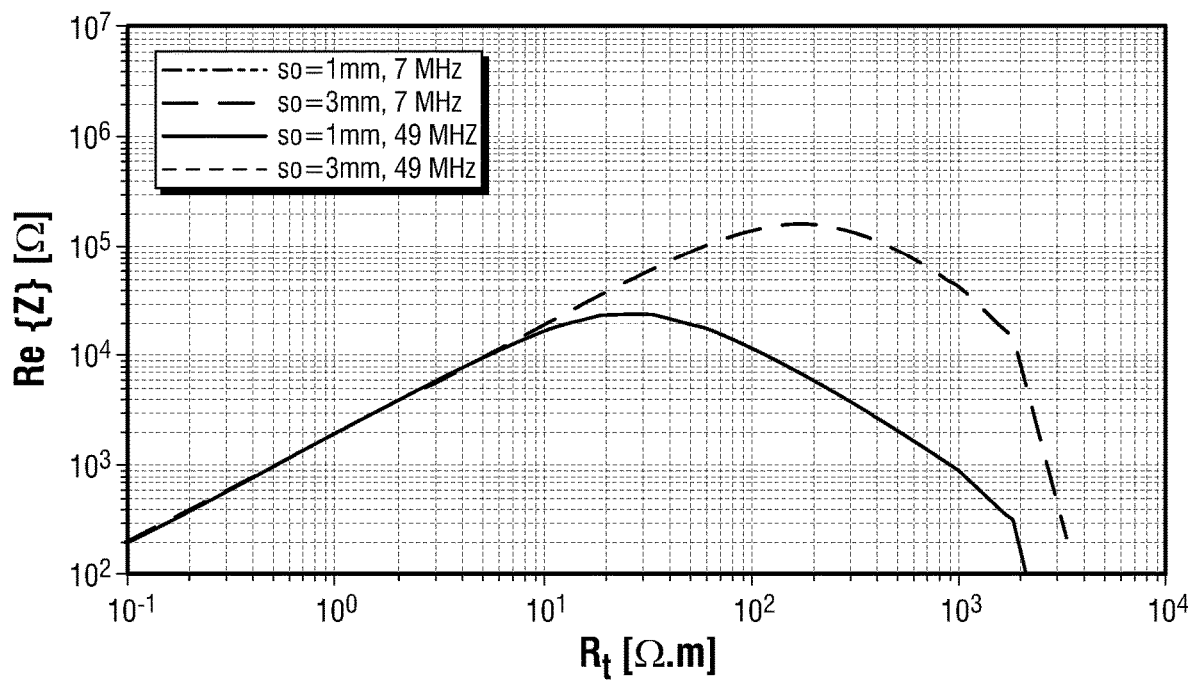
FIG. 7 illustrates an example of a graph after applying Z90 processing.

FIG. 7 illustrates a graph replotted after the application of the Z90 algorithm. As illustrated, the standoff effect may be eliminated for all frequencies utilized during data acquisition and/or processing. An ideal case using a perfect circuit model may occur where mud angle may be known and noise may not be found in data measurements, as depicted in FIG. 7. Without limitation, the proposed method below may be used with Z90 processing, but any other suitable processing or algorithms may be used.

The proposed system and method for obtaining mud properties may make use of materials that change their length in electromagnetic fields. In examples, electrostriction may be observed in all dielectric materials and respond to the square of the electric field. Electrostriction is the mechanical strain that occurs in dielectric materials due to an applied magnetic field. A similar related class of materials is the piezoelectric materials. Piezoelectricity may be observed in certain, non-centrosymmetric crystal classes. With the piezoelectric effect, there may be a direct relation between the electric field and the mechanical strain. Thus, electrostriction may be described as a quadratic effect while piezoelectricity may be described as a linear effect. Examples of piezoelectric materials include crystals such as quartz and lead titanate, langasite, lithium niabate, lithium titanate and ceramics such as barium titanate and lead zirconate titanate.

An analogous phenomenon may occur for magnetic materials in the presence of an applied magnetic field. Ferromagnetic materials may experience a mechanical strain due to the magnetic field, which leads them to stretch in the direction of the field. This is called magnetostriction and it may be described as a quadratic effect as is the case in electrostriction. In contrast, piezomagnetism may occur in antiferromagnetic materials and may be described as a linear effect. Without limitation, any material that may convert an electromagnetic field to a mechanical strain may be used for the purposes of this disclosure.

Figure 8:
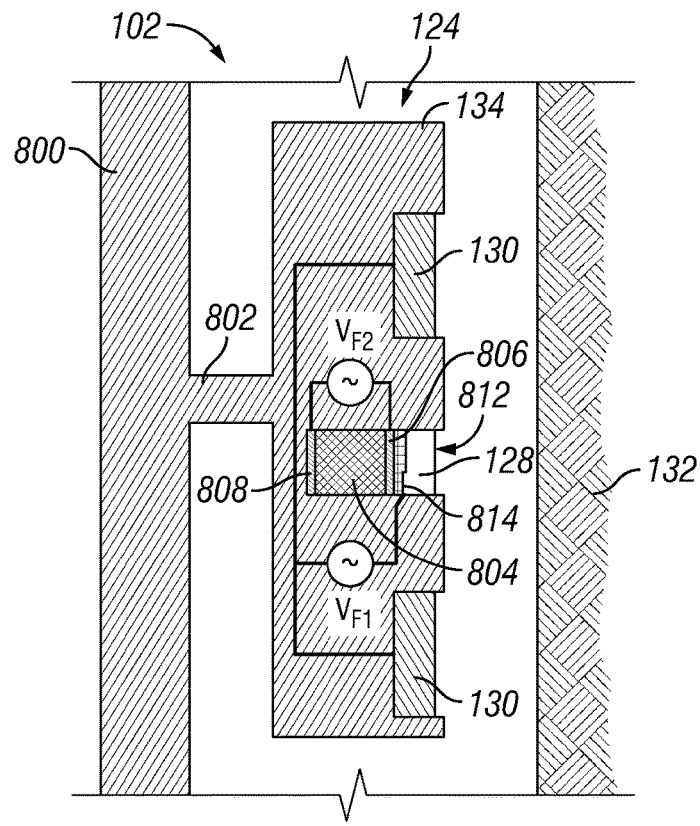
FIG. 8 illustrates an example of an electromagnetic imaging tool.

As illustrated in FIG. 8, downhole tool 102 may be disposed in borehole 124. Downhole tool 102 may include a pad 134, which may be attached to mandrel 800 by at least one arm 802. Pad 134 may be disposed at any suitable distance from formation 132 within borehole 124. It should be noted that pad 134 may attach to mandrel 800 as illustrated in FIGS. 1 and 3 by at least two arms. In examples, mandrel 800 is the body of downhole tool 102 that forms a structure for at least one arm 802 to attach to. As illustrated in FIG. 8, pad 134 may include button array 128, which may be disposed over a piezoelectric material 804. In addition, pad 134 may include at least one return electrode 130.

During operations, an electric field may be applied to piezoelectric material 804 by a set of parallel plates which may include a first plate 806 and a second plate 808. In examples, a potential difference may be applied to first plate 806 and/or second plate 808 by a voltage source, identified as $V_{F2}$. The potential difference may cause piezoelectric material 804 to compress and/or expand. The expansion and/or compression of piezoelectric material 804 may cause first plate 806 and/or second plate 808 to move with the compress and/or expansion of piezoelectric material 804. As illustrated, button array 128 may be disposed on first plate 806. It should be noted that a substrate 810 may act as a buffer and support structure for button array 128 to attach to first plate 806. In examples, first plate 806 and second plate 808 may be interchangeable. As piezoelectric material 804 expands and/or contract, first plate 806 may move in the direction of the expansion and/or contract, which may also move button array 128. In examples, second plate 808 may also move in the direction of the expansion and/or contraction of piezoelectric material 804.

During measurement operations, voltage variation may be measured as sinusoidal in time with a frequency indicated by $V_{F2}$. In examples, oil based mud imagers may operate at very high frequencies in the MHz range (0.1 to 100 MHz) and frequency measurements from downhole tool 102 may be identified as $V_{F1}$. This illustrates the difference between measurement frequency and biasing frequency. In examples, downhole tool 102 may be multi-frequency devices. Thus, mud measurements should be made at each downhole tool 102 may operate to account for the variation of mud angle with frequency. Frequency of biasing voltage may be significantly different than the operating frequency/frequencies of downhole tool 102 to avoid interference between the measurements and the circuitry that may be used to bias piezoelectric material 804.

Another consideration for the operational frequency of the biasing circuit may be the logging speed of downhole tool 102. For example, if the speed of downhole tool 102 may be about 30 ft/min (about 30 m/min) and depth sampling interval is 0.1 inches (0.254 mm) (a common logging speed and sampling rate), downhole tool 102 may take about 30 measurement samples for each button array 128 every second. Note that this depth sampling rate may be generally based on the vertical resolution of downhole tool 102 and may be in the same order with the vertical resolution. It may be desired (though not necessary), to have the biasing frequency (Such as 10 Hz.) in the same order with this sampling rate or less to not overextend the straining capabilities of piezoelectric material 804 and to have a more uniformly sampled standoff variation as button array 128 moves in conjunction with piezoelectric material 804. This operating frequency may also be different than the frequency of downhole tool 102 operation previously described and may be eliminated to a great degree with filtering circuits (not illustrated).

Without limitation, it may be possible to make two mud measurements at a single depth corresponding to different standoffs for mud angle determination. However, in practice more measurements may reduce noise and yield better results. Therefore, during measurement operations button array 128, disposed on top piezoelectric material 804, may make measurements faster than the logging speed of downhole tool 102 such that a relatively large number of measurements may be made without increasing movement of downhole tool 102. For example, mud measurements may be made at each 1/3000 seconds such that 100 mud measurements may be made for each depth location according to the measurement operations described above.

It should be noted that term "the same depth" or "single depth" may overlap designated measurement areas. For example, during measurement operations downhole tool 102 may be in motion, thus, no two different standoff samples may correspond to the exact same depth. However, as long as the samples are taken in a depth interval in the order or less of the vertical resolution of downhole tool 102, it may be assumed that the change in the formation properties may be negligible and downhole tool 102 is measuring the same properties in formation 132 (e.g., referring to FIG. 1). In other examples, the sampling interval for mud measurements may be kept at even shorter intervals than the depth sampling interval of the image created by downhole tool 102 to further enforce that the depth may be constant between mud measurements. For instance, in the example previously described, downhole tool 102 may only make 10 measurements with 1/3000 second periods and may be idle 90% of the time. To denote these limitations in achieving the same depth, the term "the same depth under practical considerations" may be used.

Additionally, it should be noted that mud measurements may be made at the operating frequency of downhole tool 102, which may be unrelated to the biasing frequency that determines the standoff variation between different instances of measurements. It is should also be noted that mud angle measurements may not be needed to be made at every depth. Properties of the mud in a borehole 124 may be constant over depth with mud impedance having a weak dependence on temperature and pressure. This may reduce the amount of data which may be transmitted to the surface. In some examples, a downhole storage module may be available. In those instances, downhole tool 102 may transmit data only at certain depths with the rest of the data being kept to be analyzed in post processing.

With continued reference to FIG. 8, during operations, button array 128 may be situated in a recess 812 to minimize the wear and tear. Recess 812 may have a length that may be equal to the maximum length of strain (e.g., expansion) that may be expected with the application of the electric field to piezoelectric material 804. Additionally, for at least a portion of button array 128, an insulator 814 may separate button array 128 from piezoelectric material 804. As noted above, insulator 814 may act as a structural support upon which button array 128 and piezoelectric material 804 may attach. During operations, as an electric field is applied to piezoelectric material 804 the piezoelectric material 804 may at least partially be disposed in recess 812. It should be noted that insulator 814 and button array 128 may traverse recess 812 by following a groove (not illustrated). The grove may minimize the friction, stabilize, and guide the movement of insulator 814 and button array 128. It should be noted that during measurement operations mud (e.g., borehole fluid) may at least partially fill a void in recess 812 which may not be filled with insulator 814 and button array 128. Generally, mud has a low friction constant, which may prevent mud from impeding the movement of insulator 814 and button array 128.

During measurement operations, downhole tool 102 may take a mud angle measurement be by taking a difference measurement at two different standoffs. These two different standoffs may be made as far apart as possible to get the (differential) mud signal as large as possible. In regards to the example using piezoelectric material 804 (e.g., referring to FIG. 8), this process may be accomplished when the sinusoidal signal attains its maximum and minimum value. In which case, a signal generator 816 and a measuring circuit 818 may be synchronized. In examples, synchronization may be defined as when measuring circuit 818 may include a biasing frequency F2 to make measure instances where signal generator 816 is at a maximum or a minimum. Signal generator 816 may generate a signal at any frequency and measuring circuit 818 may measure the signal at the frequency created by signal generator 816.

In Equation (2), formation contribution may be assumed to be independent of the standoff of the measurement button to a good approximation. Then, difference of impedance measurements at the two standoffs ($so_2$ and $so_1$) may be written as:

$$Z_{BF}(so_2) - Z_{BF}(so_1) \approx Z_{mud}(so_2) - Z_{mud}(so_1) \approx Z_{mud}(so_1) \times \left(\frac{so_2 - so_1}{so_1}\right) \quad (5)$$

In Equation (5), the mud impedance may be directly proportional to the standoff is seen in Equation (5). It should be noted that this may be the basis for mud removal algorithms that make use of the mud angle. It may be seen that the final quantity may be a scaled version of the mud impedance at a first standoff and/or a second standoff, which may have the same mud angle with it. This is expressed in Equation (6).

$$\angle Z_{mud} \approx \angle (Z_{BF}(so_2) - Z_{BF}(so_1)) \quad (6)$$

In examples, a large number of standoff measurements at a particular depth point may be made. An average of all such measurements may be found and subtracted from all the measurements. If a measurement sampling may be performed uniformly during measurement operation than an average may give the contribution of the formation impedance to the measured impedance. If not, an impedance proportional to the mud impedance may also be included in the mean calculation along with the formation impedance, which may not change results from both situations. In other examples, a median calculation may be made instead of mean to better account for large outliers. The outlined procedure using a median operation may be found in Equation (7). In Equation (7), an arrow is used above the ZBF to denote it is a vector consisting of multiple measurements. Outliers may also be thrown out based on some threshold based on the average impedance or by sorting the impedances, for example, based on their absolute values. There may exist slight variations to the procedure described here that would be obvious to people who have read this disclosure.

$$\text{Ratio} = \text{Median} \left\{ \frac{Imag\{\vec{Z}_{BF}(so)\} - \text{Median}\{Imag\{\vec{Z}_{BF}(so)\}\}}{\text{Real}\{\vec{Z}_{BF}(so)\} - \text{Median}\{\text{Real}\{\vec{Z}_{BF}(so)\}\}} \right\}; \quad (7)$$

$$\angle Z_{mud} \approx \tan^{-1}(\text{Ratio})$$

As an example, consider the example graph in FIG. 5. Assume the frequency is fixed at 7 MHz, nominal standoff is 3 mm but due to the use of the system described in this disclosure a sinusoidal standoff variation between 2.9 mm and 3.1 mm was obtained and a total of 201 uniform samples were taken. Using the equations above, the mud angle for this case is −86.9377°. If there is no noise and measurements are 100% accurate, a crossplot of the real part and imaginary part of the impedance, (a plot of impedance in the complex plane), would appear to show the graph in FIG. 9. In this ideal scenario, mud angle may be calculated directly by taking the difference of any two measurements, or using Equation (7).

Figure 9:
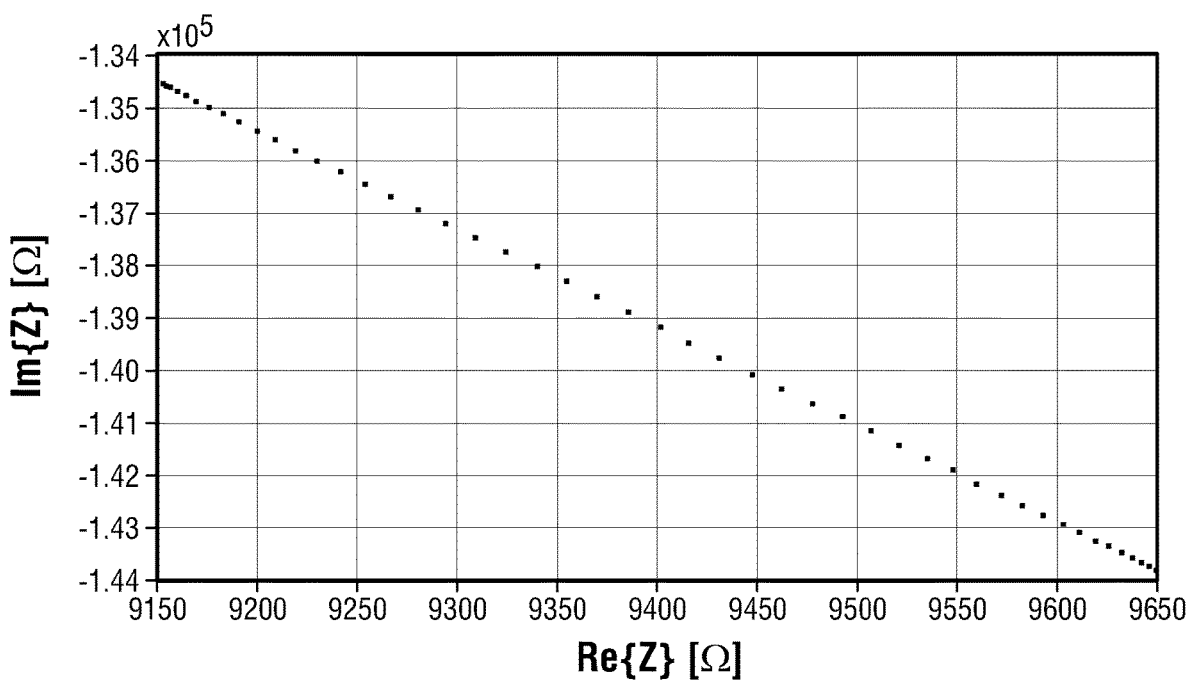
FIG. 9 illustrates an example of a graph of the measured impedance in the complex plane.
Figure 10:
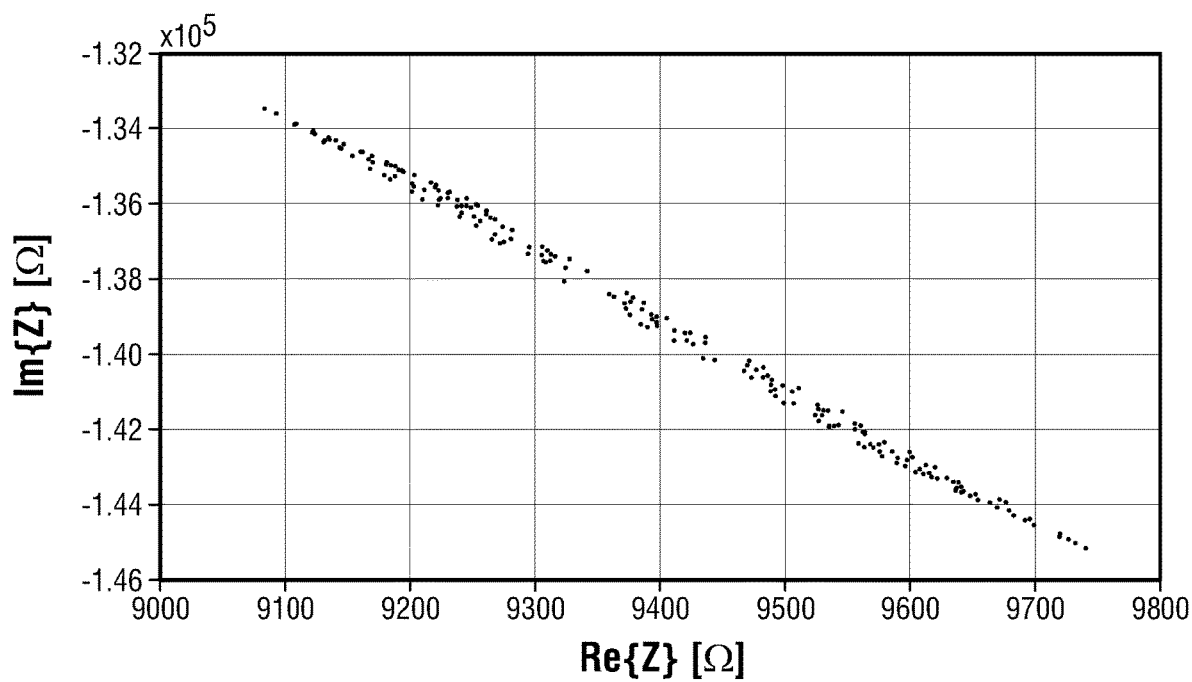
FIG. 10 illustrates an example of a graph of the measured impedance in the complex plane.
Figure 11:
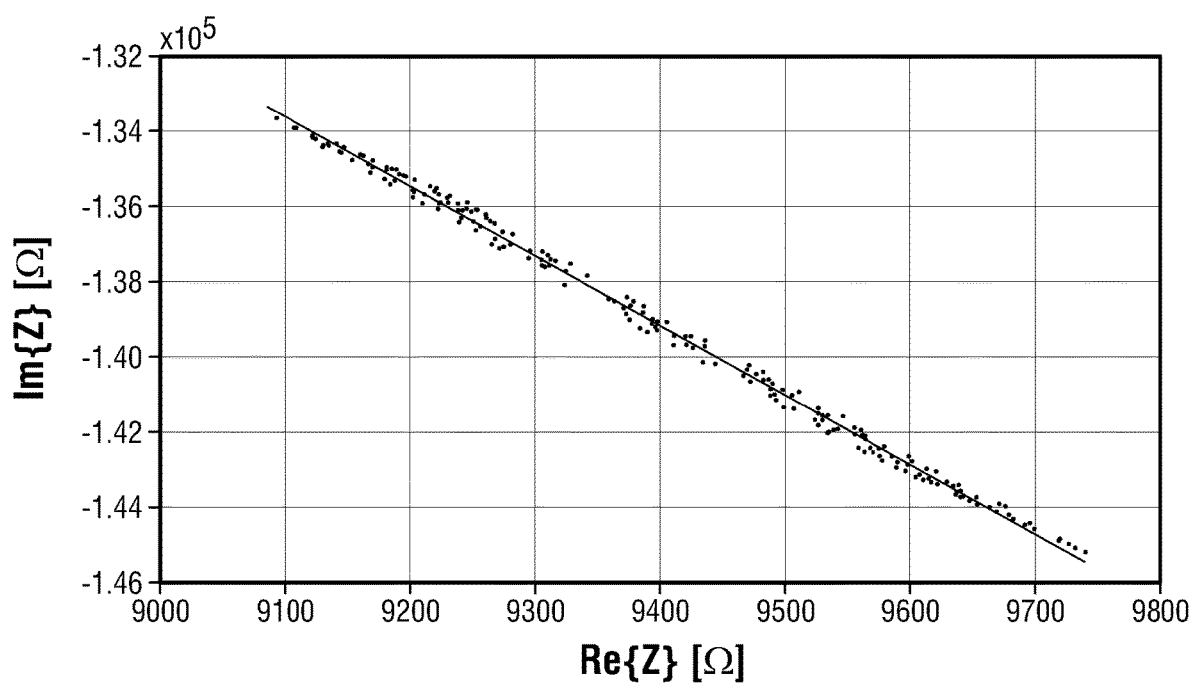
FIG. 11 illustrates an example of a graph of the measured impedance in the complex plane.

FIG. 10 illustrates a more realistic example by adding a 2% random, multiplicative noise the results depicted in FIG. 9. In this example, Equation (7) gives a mud angle of −86.9068° which is about the theoretical value. In a variant of this method, a line fit may be applied to the plot of the impedance data in the complex plane. Measuring the slope of the graphed line may give the mud angle. In examples, line fit operations may be applied using any commonly known methods, for example the fit that minimizes the least squares error between the line and the measurements may be selected. In FIG. 11, results of such a fit to the data depicted in FIG. 10 are shown. Mud angle calculated from the slope of the line in FIG. 11 is −86.8954°, which may be about the actual value.

In another example of operations, if the sampling rate is above the Nyquist rate of the biasing frequency, that is the sampling rate is at least twice the biasing frequency, and assuming a sinusoidal variation, a curve fit may be applied to the imaginary and real parts separately. This fit may be similar to the line fit described above, but in this case, the sinusoid that best fit the real and imaginary parts in a least squares sense may be found. The ratio of the amplitudes of the sinusoids found for the real and imaginary parts may give the mud angle. Quadrant of the mud angle may be found based on the median values of the imaginary and real parts or it may be directly assumed that the mud angle lies in the fourth quadrant for an oil based mud imager. Additionally, in a similar example, an fft (Fast Fourier Transform) operation may be used to determine the amplitude of the sinusoidal variation for the real and imaginary parts.

There may also exist equivalent representations of mud angle. Tangent of the mud angle is the ratio of the imaginary and real components of the mud impedance. Thus, such a ratio may be measured in some implementations instead. Any such modifications are intended to be within the scope of this disclosure.

As previously mentioned, the mud property measurements need not be made at different depths. However, if such measurements are made, results from depths that are relatively close (such as 100 ft, though this number is dependent on the properties of the particular well) may be averaged together to further reduce noise. In such an averaging process, a quantity like the ratio defined in Equation (7) may be used instead of the angle itself to alleviate issues caused by averaging angles.

Figure 12:
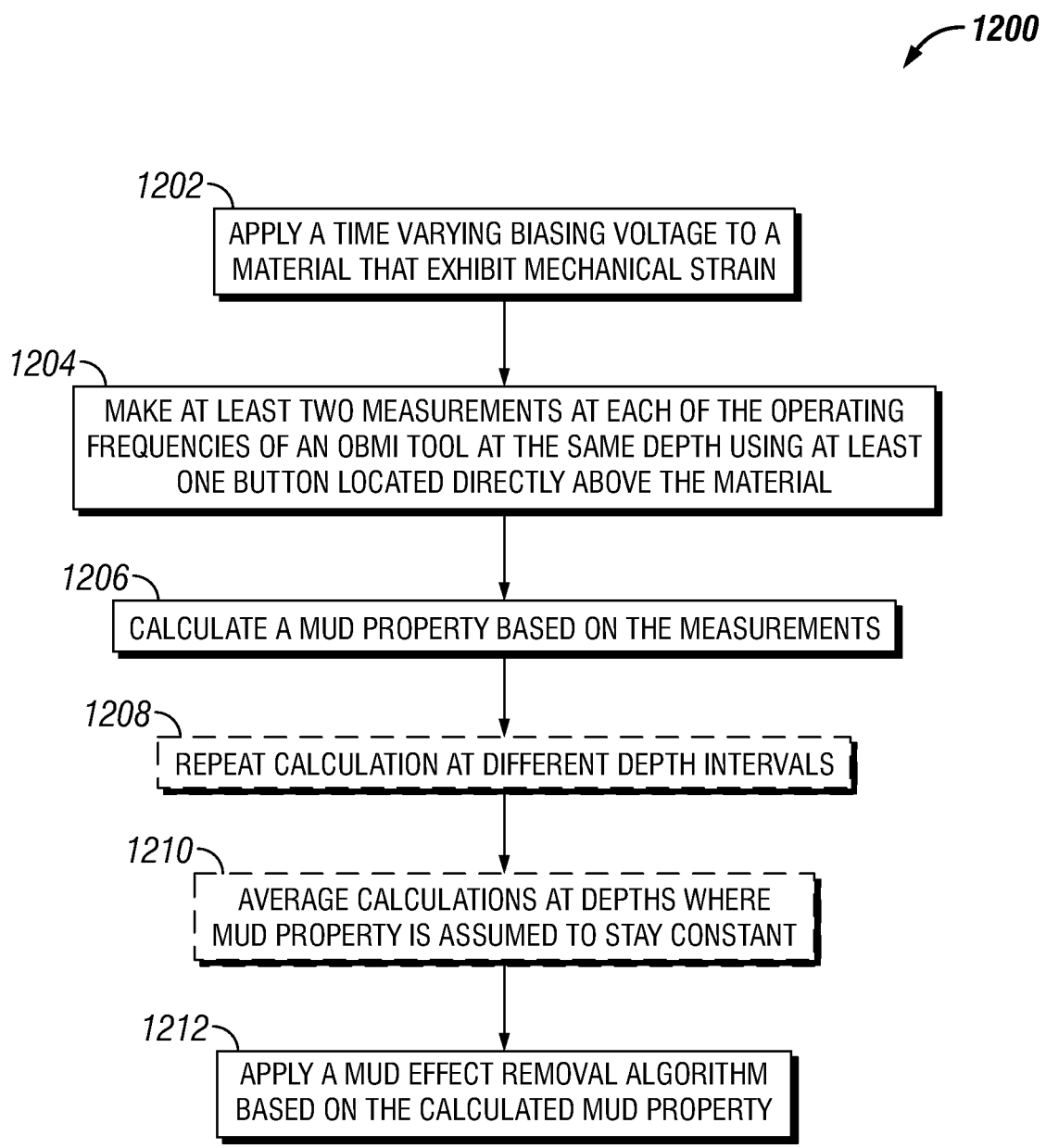
FIG. 12 illustrates an example of a workflow for calculating mud property.

FIG. 12 illustrates workflow 1200 for calculating mud property. Workflow 1200 may begin with step 1202 in which an operator may apply a time varying biasing voltage to a material that exhibit mechanical strain. For example, as discussed above, applying an electric field between first plate 806 and second plate 808 may cause piezoelectric material 804 to expand and/or contract. In step 1204 the operator may make at least two measurements at each of the operating frequencies of an oil based mud imaging tool at the same depth using at least one button array directly above the material. In examples, a first measurement may be taken before applying a voltage to the material in step 1202 and a second measurement may be taken after applying a voltage to the material in step 1202. In step 1206 the operator may calculate a mud property based on the measurements. In step 1208 the operator may repeat the calculation at different depth intervals. For example, the operator may repeat the measurements in step 1206 at different steps in borehole 124 (e.g., referring to FIG. 1) as downhole tool 102 (e.g., referring to FIG. 1) traverses borehole 124. In step 1210 the operator may average calculations at depths where mud property is assumed to stay constant. In step 1212 the operator may apply a mud effect removal algorithm (e.g. Z90, $Z_\alpha$, or the like) based on the calculated mud property.

Workflow 1200 may be utilized for downhole tool 102 (e.g., referring to FIG. 1) to calculate mud properties. In examples, button located above the piezoelectric material platform and used for measuring mud properties as detailed in this disclosure may be a part of the button array 128 (e.g., referring to FIG. 1) and they may also operate and/or function to perform imaging operations. However, in other cases, button used for measuring mud properties may be separate from the button array 128, and it may not be used for imaging purposes. This may be true in cases where the extra space needed for the biasing circuit and the platform which exhibits the mechanical strain due to an applied electromagnetic field may be fitted in a location separate from button array 128. Additionally, in other examples, more than one mud measurement button may be located on piezoelectric material 804 platform or some other components of pad 134 such as return electrodes 130, which may be disposed over the piezoelectric platform 804 in addition to mud measurement button or buttons. Such designs may be easier to implement mechanically.

Figure 13:
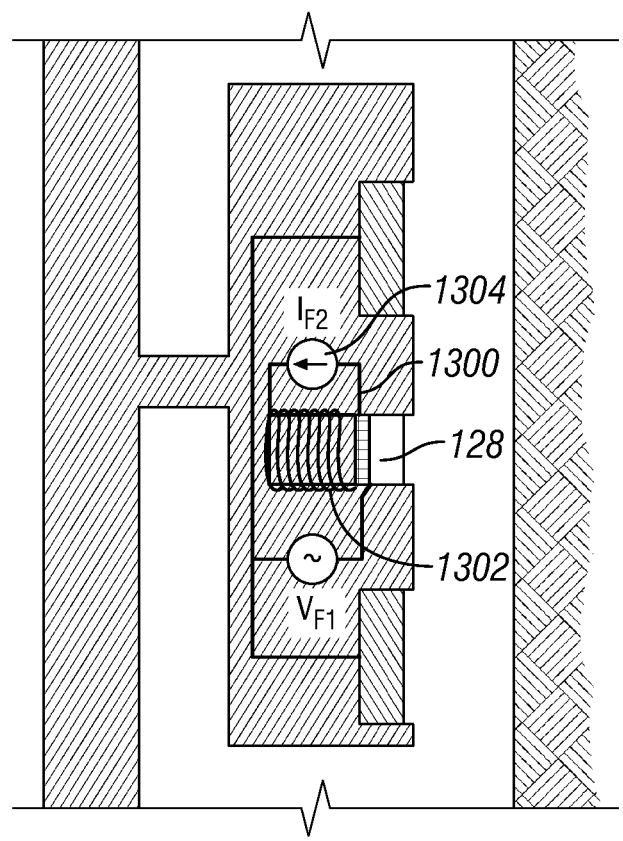
FIG. 13 illustrates another example of an electromagnetic imaging tool.

As previously mentioned, materials that may be used for creating the standoff variation and in place of piezoelectric material 804 may include electrostrictive, magnetostrictive and piezoelectric materials in addition to the piezoelectric material shown. Biasing system using an electrostrictive material would be exactly the same as those with the piezoelectric material as indicated in FIG. 8, with the piezoelectric material replaced with the electrostrictive material. In examples, there may be some minor changes in the biasing system for piezomagnetic/magnetostrictive materials as shown in FIG. 13. In such an example, mechanical strain is obtained with an applied magnetic field. Such a magnetic field may be obtained in the simplest sense by wrapping a solenoid 1300 around material 1302. When a time varying current source 1304 is connected to the terminals of the solenoid, the length of material 1302 may be changed as the magnetic field changes, thus changing the standoff of button array 128. In practice, current sources may be obtained with a voltage source in series with a large resistor. In examples, time variation of the current source may be sinusoidal. Considerations for the selection of the frequency of the biasing circuit will be similar to those described for piezoelectric material 804, described in FIG. 8 above.

The systems and methods may include any of the various features of the systems and methods disclosed herein, including one or more of the following statements.

Statement 1. A downhole tool may comprise a mandrel, wherein the mandrel is a structural support for the downhole tool; one or more arms, wherein the one or more arms are attached to the mandrel; a pad, wherein the pad is connected to the one or more arms, wherein the pad comprises: a material, where the material expands or contracts from an external electromagnetic field; an insulator, wherein the insulator is connected at a first end to the material; and an electrode, wherein the electrode is connected to the insulator.

Statement 2. The downhole tool of statement 1, wherein the material is a piezoelectric material or an electrostrictive material.

Statement 3. The downhole tool of statements 1 or 2, wherein the external electromagnetic field is an electric field or a magnetic field.

Statement 4. The downhole tool of statements 1-3, wherein the pad further comprises a first plate and a second plate, wherein the first plate is disposed between the insulator and the material.

Statement 5. The downhole tool of statement 4, wherein the first plate and the second plate are connected to a voltage source.

Statement 6. The downhole tool of statement 5, wherein an electric field is created between the first plate and the second plate by the voltage source.

Statement 7. The downhole tool of statements 1-4, wherein the pad further comprises a solenoid, wherein the solenoid is disposed around the material.

Statement 8. The downhole tool of statement 7, wherein the solenoid is connected to a current source.

Statement 9. The downhole tool of statement 8, wherein the current source induces a magnetic field with the solenoid.

Statement 10. The downhole tool of statements 1-4 and 7, wherein the pad further comprises one or more return electrodes.

Statement 11. The downhole tool of statements 1-4, 7, and 10, wherein the pad further comprises a recess and the electrode and the insulator are disposed in the recess.

Statement 12. A method for determining property of a borehole fluid comprising: applying a time varying biasing voltage to a material, wherein the material exhibits mechanical strain; taking a first measurement and a second measurement with at least one operating frequency with an electrode; calculating a mud property based at least in part on the first measurement and the second measurement; and applying a mud effect removal algorithm to the mud property.

Statement 13. The method of statement 12, further comprising repeating the first measurement and the second measurement at one or more locations in a borehole.

Statement 14. The method of statements 12 or 13, further comprising averaging the first measurement and the second measurement at the one or more locations in the borehole, wherein the mud property is constant.

Statement 15. A method for determining property of a borehole fluid comprising: disposing a downhole tool into a borehole at a first location, wherein the downhole tool comprises: a mandrel, wherein the mandrel is a structural support for the downhole tool; one or more arms, wherein the one or more arms are attached to the mandrel; a pad, wherein the pad is connected to the one or more arms, and wherein the pad comprises: a material, where the material expands or contracts from an external electromagnetic field; an insulator, wherein the insulator is connected at a first end to the material; and an electrode, wherein the electrode is connected to a second end of the material; and taking a first measurement with the electrode with at least one operating frequency; applying an external electromagnetic field to the material, wherein the material expands or contracts from the external electromagnetic field; taking a second measurement with the electrode with at least one operating frequency; calculating a mud property based at least in part on the first measurement and the second measurement; and applying a mud effect removal algorithm to the mud property.

Statement 16. The method of statement 15, further comprising repeating the first measurement and the second measurement at one or more locations in the borehole.

Statement 17. The method of statements 15 or 16, further comprising averaging the first measurement and the second measurement at the one or more locations in the borehole wherein the mud property is constant.

Statement 18. The method of statements 15-17, wherein the material is a piezoelectric material or an electrostrictive material Statement 19. The method of statements 15-18, wherein the external electromagnetic field is an electric field or a magnetic field Statement 20. The method of statements 15-19, wherein the pad further comprises a first plate and a second plate, wherein the first plate is disposed between the insulator and the material, wherein the first plate and the second plate are connected to a voltage source, and wherein an electric field is created between the first plate and the second plate by the voltage source.

Although the present disclosure and its advantages have been described in detail, it should be understood that various changes, substitutions and alterations may be made herein without departing from the spirit and scope of the disclosure as defined by the appended claims. The preceding description provides various examples of the systems and methods of use disclosed herein which may contain different method steps and alternative combinations of components. It should be understood that, although individual examples may be discussed herein, the present disclosure covers all combinations of the disclosed examples, including, without limitation, the different component combinations, method step combinations, and properties of the system. It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present examples are well adapted to attain the ends and advantages mentioned as well as those that are inherent therein. The particular examples disclosed above are illustrative only, and may be modified and practiced in different but equivalent manners apparent to those skilled in the art having the benefit of the teachings herein. Although individual examples are discussed, the disclosure covers all combinations of all of the examples. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative examples disclosed above may be altered or modified and all such variations are considered within the scope and spirit of those examples. If there is any conflict in the usages of a word or term in this specification and one or more patent(s) or other documents that may be incorporated herein by reference, the definitions that are consistent with this specification should be adopted.

What is claimed is:

1. A downhole tool comprising:
   a mandrel, wherein the mandrel is a structural support for the downhole tool;
   one or more arms, wherein the one or more arms are attached to the mandrel;
   a pad, wherein the pad is connected to the one or more arms, wherein the pad comprises:
   a material, where the material expands or contracts from an external electromagnetic field;
   an insulator, wherein the insulator is connected at a first end to the material; and
   an electrode, wherein the electrode is connected to the insulator and the electrode moves as the material expands or contracts for at least two different standoff measurements.

2. The downhole tool of claim 1, wherein the material is a piezoelectric material or an electrostrictive material.

3. The downhole tool of claim 1, wherein the external electromagnetic field is an electric field or a magnetic field.

4. The downhole tool of claim 1, wherein the pad further comprises a first plate and a second plate, wherein the first plate is disposed between the insulator and the material.

5. The downhole tool of claim 4, wherein the first plate and the second plate are connected to a voltage source.

6. The downhole tool of claim 5, wherein an electric field is created between the first plate and the second plate by the voltage source.

7. The downhole tool of claim 1, wherein the pad further comprises a solenoid, wherein the solenoid is disposed around the material.

8. The downhole tool of claim 7, wherein the solenoid is connected to a current source.

9. The downhole tool of claim 8, wherein the current source induces a magnetic field with the solenoid.

10. The downhole tool of claim 1, wherein the pad further comprises one or more return electrodes.

11. The downhole tool of claim 1, wherein the pad further comprises a recess and the electrode and the insulator are disposed in the recess.

12. A method for determining property of a borehole fluid comprising:
    applying a time varying biasing voltage to a material, wherein the material exhibits mechanical strain to move an electrode;
    taking a first measurement at a first standoff and a second measurement at a second standoff with at least one operating frequency with the electrode;
    calculating a mud property based at least in part on the first measurement and the second measurement; and
    applying a mud effect removal algorithm to the mud property.

13. The method of claim 12, further comprising repeating the first measurement and the second measurement at one or more locations in a borehole.

14. The method of claim 13, further comprising averaging the first measurement and the second measurement at the one or more locations in the borehole, wherein the mud property is constant.

15. A method for determining property of a borehole fluid comprising:
    disposing a downhole tool into a borehole at a first location, wherein the downhole tool comprises:
    a mandrel, wherein the mandrel is a structural support for the downhole tool;
    one or more arms, wherein the one or more arms are attached to the mandrel;
    a pad, wherein the pad is connected to the one or more arms, and wherein the pad comprises:
    a material, where the material expands or contracts from an external electromagnetic field;
    an insulator, wherein the insulator is connected at a first end to the material; and
    an electrode, wherein the electrode is connected to a second end of the material and the electrode moves as the material expands or contracts;
    taking a first measurement at a first standoff with the electrode with at least one operating frequency;
    applying an external electromagnetic field to the material, wherein the material expands or contracts from the external electromagnetic field;
    taking a second measurement at a second standoff with the electrode with at least one operating frequency;
    calculating a mud property based at least in part on the first measurement and the second measurement; and
    applying a mud effect removal algorithm to the mud property.

16. The method of claim 15, further comprising repeating the first measurement and the second measurement at one or more locations in the borehole.

17. The method of claim 16, further comprising averaging the first measurement and the second measurement at the one or more locations in the borehole wherein the mud property is constant.

18. The method of claim 15, wherein the material is a piezoelectric material or an electrostrictive material.

19. The method of claim 15, wherein the external electromagnetic field is an electric field or a magnetic field.

20. The method of claim 15, wherein the pad further comprises a first plate and a second plate, wherein the first plate is disposed between the insulator and the material, wherein the first plate and the second plate are connected to a voltage source, and wherein an electric field is created between the first plate and the second plate by the voltage source.

21. A downhole tool comprising:
    a mandrel, wherein the mandrel is a structural support for the downhole tool;
    one or more arms, wherein the one or more arms are attached to the mandrel;
    a pad, wherein the pad is connected to the one or more arms, wherein the pad comprises:
    a material, where the material expands or contracts from an external electromagnetic field;
    an insulator, wherein the insulator is connected at a first end to the material;
    an electrode, wherein the electrode is connected to the insulator; and
    a solenoid, wherein the solenoid is disposed around the material.

22. A downhole tool comprising:
    a mandrel, wherein the mandrel is a structural support for the downhole tool;
    one or more arms, wherein the one or more arms are attached to the mandrel;
    a pad, wherein the pad is connected to the one or more arms, wherein the pad comprises:
    a material, where the material expands or contracts from an external electromagnetic field;
    an insulator, wherein the insulator is connected at a first end to the material;
    an electrode, wherein the electrode is connected to the insulator; and a solenoid, wherein the solenoid is disposed around the material and wherein the solenoid is connected to a current source.

23. A downhole tool comprising:
a mandrel, wherein the mandrel is a structural support for the downhole tool;
one or more arms, wherein the one or more arms are attached to the mandrel;
a pad, wherein the pad is connected to the one or more arms, wherein the pad comprises:
   a material, where the material expands or contracts from an external electromagnetic field;
   an insulator, wherein the insulator is connected at a first end to the material;
   an electrode, wherein the electrode is connected to the insulator; and
a solenoid, wherein the solenoid is disposed around the material, wherein the solenoid is connected to a current source, and wherein the current source induces a magnetic field with the solenoid.

* * * * *